United States Patent [19]

Mori et al.

[11] Patent Number: 5,135,825
[45] Date of Patent: Aug. 4, 1992

[54] METHOD FOR PRODUCING AMBIENT TEMPERATURE MOLTEN SALT CONSISTING OF CERTAIN PYRIDINIUM AND IMIDAZOLIUM HALIDES AND AN ALUMINUM TRIHALIDE

[75] Inventors: Shoichiro Mori; Kazuhiko Ida; Hitoshi Suzuki, all of Ami; Setsuko Takahashi; Isao Saeki, both of Ichikawa, all of Japan

[73] Assignees: Mitsubishi Petrochemical Co., Ltd.; Nisshin Steel Co., Ltd., both of Tokyo, Japan

[21] Appl. No.: 538,652

[22] Filed: Jun. 15, 1990

[30] Foreign Application Priority Data

Jun. 22, 1989 [JP] Japan ................................. 1-158288

[51] Int. Cl.$^5$ ................... H01M 6/14; C07D 213/18; C07F 5/06
[52] U.S. Cl. .............................. 429/194; 429/199; 546/2; 546/9; 546/278; 546/347; 548/101
[58] Field of Search ............... 546/2, 9, 347, 278; 548/101; 429/194

[56] References Cited

U.S. PATENT DOCUMENTS 4,463,071  7/1984  Gifford et al. ...................... 429/194
4,463,072  7/1984  Gifford et al. ...................... 429/194

FOREIGN PATENT DOCUMENTS 60-133669  7/1985  Japan ................................. 429/194
60-133670  7/1985  Japan ................................. 429/194
62-70592   4/1987  Japan ................................. 429/194
62-70593   4/1987  Japan ................................. 429/194
62-165879  7/1987  Japan ................................. 429/194
2150739    7/1985  United Kingdom ................ 429/194

OTHER PUBLICATIONS

Chemical Abstracts, vol. 95, No. 14, p. 172, Oct. 5, 1981, G. M. Newman, et al., "Molten Salt Electrolytes for Ambient Temperature Secondary Lithium Cells", 95:118332z.

Primary Examiner—Alan L. Rotman
Attorney, Agent, or Firm—Oblon, Spivak, McClelland, Maier & Neustadt

[57] ABSTRACT

There is disclosed a method for producing an ambient temperature molten salt comprising at least one of 1,3-dialkylimidazolium halide, 1,2,3-trialkylimidazolium halide and N-alkylpyridinium halide, and an aluminum halide, which comprises suspending the above starting materials in an inert solvent having a low boiling point to carry out a complex forming reaction.

11 Claims, No Drawings

METHOD FOR PRODUCING AMBIENT TEMPERATURE MOLTEN SALT CONSISTING OF CERTAIN PYRIDINIUM AND IMIDAZOLIUM HALIDES AND AN ALUMINUM TRIHALIDE

BACKGROUND OF THE INVENTION

This invention relates to a process for producing an ambient temperature molten salt to be used as an electrolyte for a secondary battery, etc.

An ambient temperature molten salt comprising a 1,3-dialkyl- or 1,2,3-trialkylimidazolium halide or N-alkylpyridinium halide and an aluminum halide is liquid at ambient temperature, has been known to exhibit considerably high conductivity and expected greatly as a new electrolyte which is different to great extent from organic and inorganic electrolytes of the prior art.

For example, Gifford et al proposed a secondary battery comprising an ambient temperature molten salt formed from a 1,2,3-trialkylimidazolium halide and an aluminum halide as electrolyte (Japanese Provisional Patent Publications No. 3669/1985 and No. 133670/1985). Further, Furukawa et al proposed a secondary battery comprising an ambient temperature molten salt formed from 1-ethyl-3-methylimidazolium chloride and aluminum chloride as electrolyte (Japanese Provisional Patent Publication No. 165879/1987). Also, Kobayashi et al proposed a secondary battery comprising an ambient temperature molten salt formed from 1,3-dialkylimidazolium halide and a metal halide of Group IIIa of the periodic table as electrolyte (Japanese Provisional Patent Publication No. 136180/1985). Moreover, Takahashi et al proposed an electric aluminum plating method using aluminum chloride and N-butylpyridinium chloride as ambient temperature molten salts, and confirmed that the method was cheap and high stability as compared with the conventional electric aluminum plating method (Japanese Provisional Patent Publications No. 70592/1987 and No. 70593/1987).

It has been generally known that an ambient temperature molten salt composed of a 1,3-dialkyl- or 1,2,3-trialkylimidazolium halide or N-alkylpyridinium halide and aluminum chloride, for example, when an alkylimidazolium halide is exemplified, dissoviate into ions as shown by the following schemes. The ion species change with the molar ratio of the both compounds, and ion dissociation occurs as shown by the scheme (1) at a formulated molar ratio of 1:1, and as shown by the scheme (2) at a formulated molar ratio of 2:1.

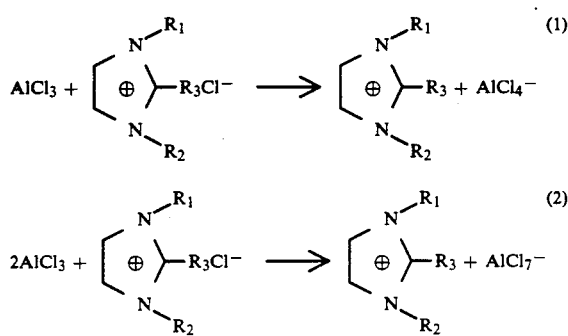

wherein $R_1$ and $R_2$ each represent lower alkyl groups, and $R_3$ represents a hydrogen atom or a lower alkyl group.

In the above example, halogen is chlorine, but similar reactions may be considered to proceed when halogen is bromine or iodine.

In the following, the step of forming an ambient temperature molten salt according to the scheme (1) or the scheme (2) from an aluminum halide and a 1,3-dialkyl- or 1,2,3-trialkylimidazolium halide or N-alkylpyridinium halide is abbreviated as the complex forming step.

In the prior art, the complex forming step is generally the solid mixing method in which an ambient temperature molten salt is produced while mixing gradually an aluminum halide which is a solid and a solid such as 1,3-dialkyl- or 1,2,3-trialkylimidazolium halide or N-alkylpyridinium halide in a glove box under $N_2$ atmosphere (for example, see Electrochemistry 54, (3), p. 257), as an example using N-butylpyridinium chloride).

The solid mixing method of the prior art in producing an ambient temperature molten salt on an industrial scale from a 1,3-dialkyl- or 1,2,3-trialkylimidazolium halide or N-alkylpyridinium halide and an aluminum halide involves some problems.

As the first point, complex forming reaction is an extremely great exothermic reaction, and it may be pointed out that heat control is extremely difficult in the solid mixing method. For example, Takahashi et al proposed a method of cooling in a dry ice-methanol bath for removal of heat (Electrochemistry, 54, (3), p. 257), but it cannot be an industrial method. This is because it may be considered that, in the solid mixing method, transmission of heat is poor to cause local heat generation, further explosive temperature elevation to occur, whereby the starting materials and (or) the product may be thermally denatured to deteriorate remarkably the characteristics of the molten salt. In fact, when the reaction amount is increased, it was observed that variance in characteristics became greater.

As the second point, for control of heat generation amount in the complex forming reaction, it may be conceivable to add little by little one of the starting materials, but since the characteristics of the molten salt are markedly deteriorated by moisture, the starting materials and the product are required to be handled under absence of moisture, and therefore handling of a small amount of a solid in dry atmosphere will obstruct markedly efficient production.

Also, as the third point, in the solid mixing method, there may be mentioned the drawback that no sufficient stirring operation can be performed to take a long time for the complex forming step.

SUMMARY OF THE INVENTION

The present inventors have investigated intensively in order to solve the problems of the complex forming step of the prior art according to the solid mixing method, and found a method for producing industrially efficiently an ambient temperature molten salt from an aluminum halide and a 1,3-dialkyl- or 1,2,3-trialkylimidazolium halide or N-alkylpyridinium halide, to accomplish the present invention.

More specifically, the present invention is characterized in that an aluminum halide and a 1,3-dialkyl- or 1,2,3-trialkylimidazolium halide or N-alkylpyridinium halide are suspended in an inert solvent having a low boiling point to carry out the complex forming reaction.

DESCRIPTION OF THE PREFERRED EMBODIMENTS

The aluminum halide to be used as the starting material in the present invention may include aluminum trichloride, aluminum tribromide and aluminum triiodide. As the 1,3-dialkyl- or 1,2,3-trialkylimidazolium halide which is one of the other starting materials, there may be included 1,3-dimethylimidazolium bromide, 1-ethyl-3-methylimidazolium chloride, 1-ethyl-3-methylimidazolium iodide, 1-n-butyl-3-methylimidazolium chloride, 1,2,3-trimethylimidazolium bromide, 1,2,3-trimethylimidazolium iodide, 1,2-dimethyl-3-ethylimidazolium bromide, 1,2-dimethyl-3-ethylimidazolium chloride, 1,2-dimethyl-3-butylimidazolium fluoride and the like. As the N-alkylpyridinium halide, there may be included N-ethylpyridinium chloride, N-ethylpyridinium bormide, N-n-butylpyridinium chloride, N-i-butylpyridinium bromide, N-n-propylpyridinium iodide, 1-ethyl-2-methylpyridinium chloride, 1-n-hexyl-2-methylpyridinium chloride, 1-n-butyl-4-methylpyridinium chloride, 1-n-butyl-2,4-dimethylpyridinium chloride, and the like.

For practicing the method of the present invention, the above-described two kinds of starting materials can be combined as desired to carry out the complex forming reaction, thereby forming the desired product. During this reaction, the molar ratio of the aluminum halide to the 1,3-dialkyl- or 1,2,3-trialkylimidazolium halide or N-alkylpyridinium halide which are the starting materials may be in the range of 0.5 to 4.5, preferably 0.7 to 4.0, more preferably 1.0 to 2.5.

As the inert solvent having a low boiling point to be used, there may be employed inert solvents having boiling points from ambient temperature to 250° C., namely solvents which do not react with the 1,3-dialkyl- or 1,2,3-trialkylimidazolium halide or N-alkylpyridinium halide, the aluminum halide and the complex thereof to damage the characteristics of the ambient temperature molten salt.

Examples of these can include saturated hydrocarbons such as n-pentane, n-hexane, n-heptane, isooctane, cyclohexane, methylcyclohexane, decalin, etc.; aromatic hydrocarbons such as benzene, toluene, xylene, ethylbenzene, cumene, tetralin, etc.; cyclic ethers such as tetrahydrofuran, 2-methyltetrahydrofuran, etc.; glymes such as dimethoxyethane, diethoxyethane, diethylene glycol dimethyl ether, etc. Among these inert solvents, saturated or aromatic hydrocarbons are preferred, which are also industrially available at low cost.

An amount of the solvent to be used is not particularly limited, but considering (1) sufficient controlling in heat generation, (2) workability during preparation and (3) efficient utilization of a reaction vessel (vessel efficiency), it is preferred in terms of weight ratio 0.5 to 5 based on 1,3-dialkyl or 1,2,3-trialkylimidazolium halide or N-alkylpyridinium halide.

The method of the present invention produces an ambient temperature molten salt by controlling the reaction temperature to utilize evaporation latent heat of the low boiling point solvent and permitting the complex forming reaction to proceed sufficiently, while suspending an aluminum halide and a 1,3-dialkyl or 1,2,3-trialkylimidazolium halide or N-alkylpyridinium halide in an inert solvent, and thereafter evaporating the inert solvent.

In the following, an example of specific method is to be described.

By use of cyclohexane as the inert solvent, in a reaction vessel containing a 1,3-dialkyl- or 1,2,3-trialkylimidazolium halide or N-alkylpyridinium halide suspended therein, an aluminum halide is gradually added under dry atmosphere. During this operation, the complex forming reaction proceeds rapidly following the above reaction scheme (1) or (2), but since considerable heat generation is accompanied by, the temperature is controlled so that the temperature within the reaction vessel may not be abruptly elevated by passing an appropriate coolant through an external jacket or an internal coil of the reaction vessel. The reaction temperature at this time is controlled preferably in the range from room temperature to 100° C. When addition of the aluminum halide is completed, while controlling thus heat generation, the complex forming reaction is completed by controlling the temperature within the system in the range from 30° to 100° C.

Then, the system is internally reduced in pressure to evaporate the inert solvent out of the system at the temperature in the range from 30° to 100° C. and to obtain the desired molten salt. Also, when an inert solvent is used in a mixture with the electrolyte, evaporation of the inert solvent can be omitted and the reaction mixture can be used as such.

As the method for controlling the exothermic reaction during addition of the aluminum halide, the method of heat removing method by utilizing the vaporization latent heat of the low boiling point solvent can be employed either singly or in combination. As a variation of the method of the present invention, the method of reversing the addition order, namely suspending an aluminum halide in cyclohexane and adding a 1,3-dialkyl- or 1,2,3-trialkylimidazolium halide or N-alkylpyridinium halide is also practicable.

By employment of the method of the present invention, it becomes possible to produce a molten salt having stable characteristics as the electrolyte rapidly and with easier control of the reaction heat.

EXAMPLES

The present invention is described in more detail below by referring to Examples and Comparative examples.

EXAMPLE 1

Into a reaction vessel made of glass equipped with a stirrer replaced with $N_2$ gas were introduced 120 g of cyclohexane and 71 g (0.484 mole) of 1-ethyl-3-methylimidazolium chloride, and 129 g (0.968 mole) of aluminum trichloride was added gradually under sufficient stirring condition so that the liquid temperature was not elevated to 60° C. or higher. After addition of the total amount, when abrupt heat generation ceased, the reaction vessel was externally heated and the mixture was stirred at 60° C. for 1.0 hour to complete the complex forming reaction. At this point, the reaction mixture became a uniform and dark green to dark brown solution. Then, the reaction vessel was gradually internally reduced in pressure while heating the reaction mixture to 50° C. to remove cyclohexane, to obtain 200 g of a molten salt. The state of the reaction mixture did not substantially change even after evaporation of cyclohexane, and the molten salt obtained was liquid, and its conductivity was measured to be 13.5 mS/cm at 25° C.

Further, when substantially similar operations were repeated to produce 3 lots of molten salts, the conduc-

EXAMPLE 2

The same reaction vessel as in Example 1 was provided with a reflux pipe, and 35.5 g (0.242 mole) of 1-ethyl-3-methylimidazolium chloride was charged together with 80 g of toluene and 40 g of n-hexane, and the system was replaced internally with $N_2$ gas. When 64.5 g (0.484 mole) of aluminum trichloride was added little by little into the reaction vessel, the temperature in the reaction vessel was elevated with accompaniment of the progress of the complex forming reaction, and n-hexane began to be refluxed at 68° C. Aluminum trichloride was thrown stepwise in predetermined amounts under the reflux condition of n-hexane, and then the reaction was completed by stirring for 30 minutes. When a similar uniform solution as in Example 1 was obtained, n-hexane was evaporated under an atmosphere, and the system was internally gradually reduced in pressure to evaporate toluene.

The molten salt formed exhibited the same appearance as in Example 1, exhibiting a conductivity of 13.7 mS/cm at 25° C.

EXAMPLE 3

A molten salt was prepared according to the same procedure as in Example 1 except for using 49.6 g (0.242 mole) of 1,2-dimethyl-3-ethylimidazolium bromide and 64.5 g (0.484 mole) of aluminum trichloride. The molten salt formed was a uniform solution, and had a conductivity of 6.5 mS/cm at 25° C.

EXAMPLE 4

When the same reaction as in Example 1 was practiced except for using n-heptane in place of cyclohexane, a molten salt with a conductivity of 13.8 mS/cm at 25° C. was obtained.

EXAMPLE 5

A molten salt was prepared according to the same procedure as in Example 1 except for using 33.5 g (0.233 mole) of N-ethylpyridinium chloride and 62 g (0.465 mole) of aluminum trichloride. The molten salt formed was a uniform solution, and had a conductivity of 10.1 mS/cm at 25° C.

EXAMPLE 6

A molten salt was prepared according to the same procedure as in Example 1 except for using 80 g (0.466 mole) of N-butylpyridinium chloride and 120 g (0.930 mole) of aluminum trichloride. The molten salt formed was a uniform solution, and had a conductivity of 7.3 mS/cm at 25° C.

COMPARATIVE EXAMPLE

When 35.5 g (0.242 mole) of 1-ethyl-3-methylimidazolium chloride was placed in a glass vessel and 64.5 g (0.484 mole) of aluminum trichloride was gradually added, the reaction occurred gradually to be partly changed into solution state. At this time, abrupt exothermic reaction accompanied with the reaction was observed. Then, the vessel was cooled to maintain the reaction temperature not to elevate more than 60° C. After the total amount of aluminum trichloride was thrown, the reaction mixture was heated at 60° C. for one hour. After cooling, conductivity was measured at 25° C. to be 10.8 mS/cm. When the same reaction was repeated again, the conductivity was found to be 11.7 mS/cm (25° C.).

According to the method of Comparative example, the characteristic such as conductivity of the molten salt was found to be low, and also reproducibility of the characteristic was inferior.

We claim:

1. A method for producing an ambient temperature molten salt comprising at least one 1,3-dialkylimidazolium halide, 1,2,3-trialkylimidazolium halide, or N-alkylpyridinium halide, and an aluminum halide, which comprises suspending the above starting materials in an inert solvent having a low boiling point to carry out a complex forming reaction wherein the reaction temperature is controlled within the range of room temperature to 100° C. by utilizing the evaporation latent heat of the low boiling point solvent.

2. The method for producing an ambient temperature molten salt according to claim 1, wherein the molar ratio of the aluminum halide to at least one of the 1,3-dialkylimidazolium halide, 1,2,3-trialkylimidazolium halide or N-alkylpyridinium halide is 0.5 to 4.5.

3. The method for producing an ambient temperature molten salt according to claim 1, wherein the boiling point of the inert solvent is in the range of ambient temperature to 250° C.

4. The method for producing an ambient temperature molten salt according to claim 3, wherein the inert solvent is at least one selected from the group consisting of a saturated hydrocarbon, an aromatic hydrocarbon, a cyclic ether and a glyme.

5. The method for producing an ambient temperature molten salt according to claim 4, wherein the inert solvent is an aromatic hydrocarbon.

6. The method for producing an ambient temperature molten salt according to claim 1, wherein the reaction is carried out by adding one of the starting materials.

7. The method for producing an ambient temperature molten salt according to claim 1, wherein the 1,3-dialkylimidazolium halide or 1,2,3-trialkylimidazolium halide is selected from the group consisting of 1,3-dimethylimidazolium bromide, 1-ethyl-3-methylimidazolium chloride, 1-ethyl-3-methylimidazolium iodide, 1-n-butyl-3-methylimidazolium chloride, 1,2,3-trimethylimidazolium bromide, 1,2,3-trimethylimidazolium iodide, 1,2-dimethyl-3-ethylimidazolium bromide, 1,2-dimethyl-3-ethylimidazolium chloride and 1,2-dimethyl-3-butylimidazolium fluoride.

8. The method for producing an ambient temperature molten salt according to claim 1, wherein the N-alkylpyridinium halide is selected from the group consisting of N-ethylpyridinium chloride, N-ethylpyridinium bromide, N-n-butylpyridinium chloride, N-i-butylpyridinium bromide, N-n-propylpyridinium iodide, 1-ethyl-2-methylpyridinium chloride, 1-n-hexyl-2-methylpyridinium chloride, 1-n-butyl-4-methylpyridinium chloride and 1-n-butyl-2,4-dimethylpyridinium chloride.

9. The method for producing an ambient temperature molten salt according to claim 1, wherein the aluminum halide is selected from the group consisting of aluminum trichloride, aluminum tribromide and aluminum triiodide.

10. The method for producing an ambient temperature molten salt according to claim 5, wherein the aromatic hydrocarbon is selected from the group consisting of benzene, toluene, xylene, ethylbenzene, cumene and tetralin.

11. The method for producing an ambient temperature molten salt according to claim 1, wherein the molar ratio of the inert solvent to at least one of the 1,3-dialkylimidazolium halide, 1,2,3-trialkylimidazolium halide and N-alkylpyridinium halide is 0.5 to 5.

* * * * *